United States Patent [19]
Braatz et al.

[11] Patent Number: 5,645,832
[45] Date of Patent: Jul. 8, 1997

[54] USE OF LIPASES FOR PRODUCING DRUGS

[75] Inventors: Reinhard Braatz, Wedel; Roland Kurth, Limburgerhof; Elke Menkel-Conen, Speyer; Hansjoerg Rettenmaier, Gruenstadt; Thomas Friedrich, Darmstadt; Thomas Subkowski, Mutterstadt, all of Germany

[73] Assignee: BASF Aktiengesellschaft, Ludwigshafen, Germany

[21] Appl. No.: 422,921

[22] Filed: Apr. 17, 1995

Related U.S. Application Data

[62] Division of Ser. No. 170,358, Dec. 28, 1993, Pat. No. 5,489,530.

[30] Foreign Application Priority Data

Jul. 1, 1991 [DE] Germany .................. 41 21 704.7

[51] Int. Cl.$^6$ ................................. A61K 38/46
[52] U.S. Cl. ............ 424/94.6; 435/198; 435/253.3; 435/244
[58] Field of Search .................. 435/253.3, 198, 435/244; 424/94.6

[56] References Cited

U.S. PATENT DOCUMENTS

| | | | |
|---|---|---|---|
| 3,431,175 | 3/1969 | Arima | 435/198 |
| 3,511,753 | 5/1970 | Prave | 435/198 |
| 3,649,455 | 3/1972 | Abe | 435/198 |
| 3,875,007 | 4/1975 | Kobayashi | 435/198 |
| 4,019,959 | 4/1977 | Gawel | 435/198 |
| 4,283,494 | 8/1981 | Kokusho | 435/829 |

FOREIGN PATENT DOCUMENTS

| | | |
|---|---|---|
| 387945 | 9/1990 | European Pat. Off. . |
| 1642654 | 5/1971 | Germany . |
| 1084431 | 9/1967 | United Kingdom . |

OTHER PUBLICATIONS

"Bergey' Manual of Systematic Bacteriology". 1986, Krieg et al. pp. 362–365, Williams & Wilkins 1986.

*Primary Examiner*—Irene Marx
*Attorney, Agent, or Firm*—Keil & Weinkauf

[57] ABSTRACT

The use of bacterial lipases which show an immunological cross-reaction with the antibodies to the lipase produced by the microorganism *Pseudomonas spec.* DSM 6483 and/or *Pseudomonas cepacia* IAM 1057 for producing drugs for the therapy of maldigestion is described.

1 Claim, No Drawings

USE OF LIPASES FOR PRODUCING DRUGS

This is a divisional of application Ser. No. 08/170,358, filed as PCT/EP92/01412, on Jun. 23, 1992 now U.S. Pat. No. 5,489,530.

The present invention relates to the use of specific lipases for producing drugs.

Lipases play an important part in the digestion of fats because they catalyze the elimination of fatty acids from them. Lipases are therefore employed in therapy for treating digestive disorders based on enzyme deficiency. The latter is found, for example, in cases of pancreatic insufficiency, chronic pancreatitis and following gastric resection. The lipases used for this purpose are mostly products based on pig pancreas which has been defatted, dried and ground. However, such preparations of pig pancreas have several serious disadvantages:

1. They have a low specific activity and therefore have to be employed in an amount of up to 5–10 g per day.
2. The pH range for their activity is from 5 to 9. They therefore display no lipolytic activity on passage through the stomach.
3. Their stability is satisfactory only at pH 6 and above. They must therefore be administered either in acid-resistant form or in very high doses.
4. The lipases prepared for pharmaceutical purposes are not pure. They contain proteases and amylases and are thus contraindicated for certain forms of pathological maldigestion.

It has already been proposed to prepare lipases for the therapy of maldigestion by cultivating fungi of the genus Aspergillus, Penicillium, Mucor, Candida or Rhizopus. DE-A 16 42 654 and EP-A 387 945 describe the preparation and purification of a lipase for therapeutic purposes by fermentation of the fungus *Rhizopus arrhizus*.

The present invention relates to the use of bacterial lipases which show an immunological cross-reaction with the antibodies to the lipase produced from the microorganism *Pseudomonas spec.* DSM 6483 and/or *Pseudomonas cepacia* IAM 1057 for producing drugs for the therapy of maldigestion. *Pseudomonas spec.* was deposited on May 27, 1991, at the International Depository Authority, Deutsche Sammlung von Mikroorganismen und Zellkulturen GmbH, Mascheroder Weg 1b, D-3300, Braunschweig, Germany, as Deposit No. DSM 6535. In order to differentiate the bacterial lipases, antibodies against lipase from said microorganisms are required. The lipases can be obtained from bacteria by cultivating them in a nutrient medium, and isolating the enzyme from the culture broth. Suitable nutrient media contain sources of carbon and of nitrogen, inorganic salts and, where appropriate, small amounts of trace elements and vitamins. Nitrogen sources which can be used are inorganic or organic nitrogen compounds or materials which contain these compounds. Examples are: ammonium salts, nitrates, corn steep liquor, yeast autolysate, yeast extract and hydrolyzed casein. Carbon sources which can be used are sugars such as glucose, polyols such as glycerol or organic acids such as citric acid or fatty acids. Particularly suitable carbon sources are vegetable oils such as soybean, linseed or olive oil. Examples of inorganic salts are the salts of calcium, magnesium, manganese, potassium, zinc, copper, iron and other metals. Particularly suitable anions in the salts are phosphate and nitrate ions. The cultivation is preferably carried out at from 25° to 33° C. The pH of the medium is maintained at 6–7.5, preferably 6.5–7 using 2N sulfuric acid or ammonia to keep it constant during the fermentation. Submerged cultivation is carried out with vigorous aeration and stirring. Fermentation is continued, measuring the enzyme activity at intervals of three hours, until two consecutive measurements show constant activity. An incubation time of 40–60 hours is generally sufficient.

It is possible in this way to obtain, using bacterial strains which have been isolated directly from natural habitats, enzyme yields of 50–500 mg per 1 of culture broth. The enzyme yield can be increased by mutation with chemical agents or UV light followed by selection for improved lipase productivity.

The enzyme is removed from the culture broth in a conventional way. The broth is centrifuged or filtered to remove microorganisms and insoluble material. The liquid phase is then collected in order to obtain the lipase. This takes place by precipitation with a water-miscible organic solvent (eg. alcohol or acetone) or by adding a salt such as ammonium sulfate. The specific activity can be increased, and the content of impurities can be further reduced, by redissolving the crude product obtained in this way and reprecipitating it, for example by fractional precipitation by adding solvents or salt. Another possible way of purifying the crude product is to subject the enzyme-containing solution to ultrafiltration using suitable membranes, when low molecular weight impurities pass through the membrane but the enzyme being retained.

In order to test the lipases for their utilizability, antibodies against the lipases are required and can be obtained from *Pseudomonas spec.* DSM 6483 or *Pseudomonas cepacia* as described above. To do this, one of these lipases is injected into rabbits at intervals of 10–20 days until the antibody titer in their sera is sufficiently high. The serum obtainable in this way can be used directly in an ELISA for testing the lipases.

Examples of bacterial lipases which show an immunological cross-reaction with the abovementioned lipases are the lipase from Chromobaoter viscosum (obtainable from Immuno Biology Laboratories GmbH, 2000 Hamburg 20), that from *Pseudomonas cepacia* IAM 1057 (obtainable from Amano Pharmaceutical Co. Ltd., Nagoya, Japan), that from *Pseudomonas fluorescens* (obtainable from Enzymatix Ltd., Cambridge, UK) and that from *Pseudomonas spec.* DSM 6535.

The pH range for activity of the bacterial lipases is from 3 to 9. In addition, the bacterial lipases according to the invention are found to be inhibited distinctly less by deoxycholic acid than is the fungal lipase from *Rhizopus arrhizus*. This means that the lipolytic activity of the bacterial lipases according to the invention can be utilized with greater efficiency in the gastrointestinal tract than the products currently on the market for the therapy of maldigestion.

The products obtained by the above process have the additional advantage that the lipase concentration therein is very high so that only small amounts of substance (about 0.2 g) need to be administered. This represents a drastic improvement by comparison both with pancreatin and with fungal lipase.

Another advantage of the bacterial enzymes which may be mentioned is that the precipitates which have been described can be prepared as single products without concomitant proteolytic or amylolytic enzyme activities. This is an advantage inasmuch as, owing to the presence of proteases and amylases, pancreatin cannot be used therapeutically in every case: the amylase content is undesirable for children with mucoviscidosis, while lipases are therapeutically desirable but proteases are contraindicated in patients with acute pancreatitis or active episodes of chronic pancreatitis.

These lipases are very suitable for treating maldigestion of a variety of etiologies, ie. inadequate digestion of the intestinal contents as a consequence of enzyme deficiency (eg. after gastric resection, in cases of pancreatic insufficiency, hepatic disorders and hypocholia). The lipases are administered orally in the form of coated or uncoated tablets and other solid dosage forms. The content in the individual forms is preferably from 10,000 to 100,000 F.I.P. enzyme units (see "Pancreas Powder" monograph, Ph. Eur., 2nd Edition, Serial No. 350). The dosage per patient and day is from 20,000 to 400,000 enzyme units.

The lipases can be used in conventional solid or liquid pharmaceutical forms, eg. uncoated or (film-)coated tablets, capsules, powders, granules or solutions. These are produced in a conventional way, with the active substances being processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al., Pharmazeutische Technologie, Thieme-Verlag, Stuttgart, 1978). The content of active substance in the forms obtained in this way is normally from 10 to 90% by weight.

EXAMPLE 1 a) Preparation and purification of the lipase from *Pseudomonas spec.* DSM 6483

The following medium was used to cultivate the microorganism *Pseudomonas spec.* DSM 6483:

|  | g/l |
|---|---|
| $KH_2PO_4$ | 20 |
| $Na_2HPO_4$ | 10 |
| $MgSO_4$ | 5 |
| $CaCl_4 \times 2H_2O$ | 3 |
| $FeSO_4 \times 7H_2O$ | 0.5 |
| $MnSO_4 \times 4H_2O$ | 0.005 |
| $CoCl_2 \times 6H_2O$ | 0.005 |
| $CuSO_4 \times 5H_2O$ | 0.005 |
| $ZnSO_4 \times 7H_2O$ | 0.005 |
| Yeast extract | 5 |

The carbon source was refined soybean oil which was pumped in at a constant rate of 1 g/l×h. The pH was kept constant at 6.5 throughout the fermentation using 2N $H_2SO_4$ and 25% strength $NH_4OH$.

The seed culture was obtained by inoculating 400 ml of nutrient broth medium pH 6.5 with *Pseudomonas spec.* DSM 6483.

The seed culture was incubated in a shaker at 30° C. for 10 h.

The medium was inoculated at 30° C. and pH 6.5 with 5 parts by volume of the seed culture per 100 parts by volume of medium. The main cultivation was carried out at 30° C. in 10 l stirred fermenters containing 8 l. The incorporated paddle stirrer rotated at 1000 rpm, and the aeration rate was one volume of air per minute and volume of fermentation broth. After 60 h, the fermentation broth had a constant activity of 300 F.I.P. enzyme units in two consecutive measurements. The fermentation was then stopped, and the lipase was isolated from the fermentation broth as follows:

The discharge from the fermenter was diluted with n-propanol until the alcoholic content was 65% by volume. Biomass and precipitated by-products were removed by centrifugation. The clear alcoholic enzyme solution was concentrated under reduced pressure to one third of the initial volume. The resulting enzyme concentrate was washed with three volumes of $H_2O$ by diafiltration (cellulose triacetate crosscurrent filtration modules, separation limit 20,000 nominal molecular weight, from Sartorius, Göttingen), and then concentrated by filtration to one quarter of the initial volume. Lipase was precipitated from this aqueous enzyme concentrate by adding n-propanol to a content of a 5% by volume. The precipitate containing the lipase activity was collected by centrifugation and taken up in an aqueous solution containing 65 parts by volume of n-propanol. The ratio of precipitate to n-propanol/water mixture was 1:10 by weight.

Undissolved precipitate was removed by centrifugation. The lipase was precipitated from the clear supernatant by increasing the n-propanol content to 80 parts by volume. The precipitate was collected by centrifugation and freeze-dried. The resulting enzyme powder had a specific activity of 7100 F.I.P. units per milligram of protein.

b) Lipases can also be prepared and isolated from other pseudomonads and from Chromobacter viscosum in a similar way.

A very good lipase can be obtained from *Pseudmonas spec.* DSM 6535.

Taxonomic investigation of the strain DSM 6535 showed the following properties:

Cell morphology: diameter 0.8–1.0 μm with a length of 1.5–2.0 μm

Gram stain: negative in all growth phases

Spores: none

Motility: present

No growth at 45° C. and 41° C.

Growth at 37° C.

Growth optimum at 30° C.

Catalase: positive

Oxidase: weak positive

No fermentation of glucose

Strictly aerobic growth

The listed properties make it possible to assign DSM 6535 to the genus Pseudomonas.

It was intended to make it possible to assign the species by identifying the following physiological characteristics:

Arginine dihydrolase: present

Lysine decarboxylate: absent

Ornithine decarboxylase: absent

Pigment formation on King B medium: negative

Hydrolysis of Tween* 80: positive

Hydrolysis of casein: weak positive

Hydrolysis of gelatin: weak positive

Hydrolysis of starch: positive

Hydrolysis of urea: positive

Hydrolysis of esculin: weak positive

Reduction of nitrate to nitrite: positive

Formation of levan from sucrose: negative

Lecithinase: negative

β-Galactosidase: positive

Utilization of glucose: positive mannose: positive mannitol: positive inositol: positive N-acetylglucosamine: weak positive gluconic acid: positive citric acid: positive malic acid: negative phenylacetic acid: negative benzylamine: positive trehalose: positive The physiological properties of DSM 6535 do not make unambiguous assignment of a species possible.

Further characterization was thus attempted via the composition of fatty acids in the cell wall:

The occurrence of the following fatty acids allows DSM 6535 to be assigned unambiguously to the rRNA homology group 2 pseudomonads: 14:0 3-OH, 16:02-OH, 16:03-OH, 16:1 2-OH and 18:1 2-OH.

Comparison of the fatty acid pattern with those of phytopathogenic bacteria shows similarity to the *Pseudomonas cepacia/gladioli* complex within rRNA homology group 2.

However, the outstanding physiological feature of DSM 6535 is the lipase productivity:

Under the fermentation conditions specified above, up to 3.2 g of lipase per liter of fermentation medium can be produced with DSM 6535.

EXAMPLE 2

Preparation of the antibodies and ELISA

Equal volumes of a solution of 0.1 mg/ml antigen (=lipase from *Pseudomonas spec.* DSM 6483) and of Freund's adjuvant were mixed until a homogeneous emulsion was produced. 2 ml samples of this emulsion were injected into two female rabbits according to the following schedule:

Antigen in complete Freund's adjuvant was given on day 0. Then antigen in incomplete Freund's adjuvant was given twice at an interval of 14 days, and then antigen without adjuvant was given until the antibody titer was sufficient for the ELISA described hereinafter. The titer of the anti-*Pseudomonas spec.* DSM 6483 serum was determined in the ELISA as follows:

Step 1
Microtiter plates were coated with antigen using a solution with a concentration of 1–10 µg/ml in 0.05M $NaHCO_3$ pH 9.2.
Step 2
Excess binding sites were saturated with 1% bovine serum albumin phosphate-buffered saline (PBS).
Step 3
Microtiter wells were washed 3 times with 0.05% Tween* 20 in PBS.
Step 4
11 dilutions (factor 2) of the rabbit antiserum in PBS with 0.5% Tween* 20 were introduced.
Step 5
Washing as in step 3.
Step 6
Biotinylated anti-rabbit IgG antibody diluted 1:10,000 in 0.1% bovine serum albumin in PBS was introduced.
Step 7
Washing as step 3.
Step 8
Streptavidin-peroxidase complex was reacted with the antibody complex (dilution 1:10,000).
Step 9
Washing as step 3.
Step 10
0.42 mM tetramethylbenzidine in 0.1M Na acetate pH 4.9, containing 14.7 µl of 3% $H_2O_2$, was employed as peroxidase substrate solution.
Step 11
The enzyme reaction was stopped with 2M $H_2SO_4$.

The titer of anti-*Pseudomonas spec.* 6483 was determined by measuring the absorption at 450 nm.

All lipases which showed an immunological cross-reaction with the *Pseudomonas spec.* DSM 6483 antibodies which have been prepared as described above are lipases according to the present invention.

Typical examples of such lipases are: Lipase from Chromobacter viscosum (obtainable from Immuno Biology Laboratories GmbH, 2000 Hamburg 20), lipase from *Pseudomonas cepacia* IAM 1057 (from Amano Pharmaceutical Co. Ltd., Nagoya, Japan, obtainable under the proprietary name Amano P), lipase from *Pseudomonas fluorescens* (proprietary product of Enzymatix Ltd., Cambridge, UK) and lipase from *Pseudomonas spec.* DSM 6535.

The lipases of the present invention ought preferably also to show immunological cross-reactions with antibodies against the lipase from *Pseudomonas cepacia* IAM 1057. Properties of the lipases

EXAMPLE 3

Specific activities of various lipase preparations of microbial origin compared with pancreatin.

The activities were determined by two different methods:
1) Lipase activity determination for pancreas powder ("Pancreas Powder" monograph, Ph. Eur. 2nd Edition, Serial No. 350), enzyme assay at 37° C. pH 9, 10 mM taurocholate.
2) Activity determination for microbial lipases (Pharmaceutical Enzymes, editors: R. Ruyssen, A. Lauwers, E. Story, Scientia P.V.B.A. 1978, pp. 210–213), enzyme assay at 37° C. pH 7, 0.5 mM taurocholate.

A test kit obtained from Bio-Rad Laboratories GmbH and based on the method of M. Bradford (Anal. Biochem. (72) (1976) 248) was used for protein determination.

As Table I below shows, the specific activities measured by the method prescribed for pancreatin in the European Pharmacopoeia were distinctly higher for the bacterial lipases described here than for fungal lipases or for pancreatin. There is agreement between pancreatin and the bacterial lipases inasmuch as the specific activities of both enzymes measured at pH 9 were higher than the activities measured at pH 7 in the assay for microbial lipases.

The behavior of the fungal lipases investigated was the reverse of this, and thus their maximum specific activities cannot be compared directly with that of pancreatin.

TABLE I

| Lipase from | Specific activity per milligram of protein by the method of Pharmaceutical Enzymes | F.I.P. |
|---|---|---|
| Pseudomonas spec. DSM 6483 (Example 1) | 6696 | 7108 |
| Chromobacter viscosum | 3302 | 5352 |
| Pseudomonas cepacia (Amano P) | 738 | 1038 |
| Pseudomonas spec. DSM 6535 (Example 1) | 5064 | 6290 |
| Pancreatin | 226 | 430 |
| Rhizopus arrhizus | 942 | 317 |
| Candida cylindracea | 4597 | 41.6 |
| Mucor miehei | 294 | 169 |
| Aspergillus niger | 394 | 0 |
| Penicillium roquefortii | 195 | 83.1 |
| Geotrichum candidum | 172 | 63.9 |

EXAMPLE 4 pH-dependence of bacterial lipases compared with pancreatin

In order to examine the connection between pH and lipolytic activity, a modified system for assaying microbial and animal lipases was used (Ch. Unterberg, Fette, Seifen, Anstrichmittel, 88 (1986) 561–564). The values listed in Table II show that the bacterial lipases have a pH range for activity which is extended far into the acid region compared with pancreatin, which means that these lipases have the advantage of being able to display their activity even in the stomach.

TABLE II

| | Relative lipolytic activity (%) | | | |
|---|---|---|---|---|
| pH | Pancreatin | Amano P | Pseudomonas spec. DSM 6483 | Pseudomonas spec. DSM 6535 |
| 3.0 | 0 | 3.2 | 0 | 14.3 |
| 3.5 | 0 | 37.5 | 14.3 | 27.4 |
| 4.0 | 0 | 42.5 | 16.9 | 20.7 |
| 4.5 | 5.0 | 41.3 | 29.9 | 34.1 |
| 5.0 | 20.0 | 45.0 | 52.0 | 34.1 |
| 5.5 | 27.6 | 40.0 | 52.0 | 35.4 |
| 6.0 | 30.8 | 456.0 | 52.0 | 37.8 |
| 6.5 | 46.6 | 52.4 | 58.4 | 46.3 |
| 7.0 | 61.7 | 70.0 | 71.4 | 56.1 |
| 7.5 | 76.7 | 90.0 | 79.2 | 76.8 |
| 8.0 | 86.7 | 100.0 | 100.0 | 100.0 |
| 8.5 | 90.0 | 92.4 | 84.4 | 68.3 |
| 9.0 | 100.0 | 95.0 | 100.0 | 69.5 |

EXAMPLE 5

Effect of sodium deoxycholate on the lipases from *Pseudomonas spec.* DSM 6535 and *Rhizopus arrhizus*

In order to examine the effect of the bile salt sodium deoxycholate on the activity of microbial lipases, the method for determining the activity of pancreas powder ("Pancreas Powder" monograph, Ph. Eur., 2nd Edition, Serial No. 350) was used. In place of taurocholate, sodium deoxycholate in concentrations from 0 to 10 mM were employed in the enzyme assay.

As is clear from Table III below, the bacterial lipases according to the present invention have the following advantage compared with a fungal lipase from *Rhizopus arrhizus* used for comparison:

In particular, the lipase from *Pseudomonas spec.* DSM 6535 is not inhibited at sodium deoxycholate concentrations above 5 mM, whereas the fungal enzyme shows marked inactivation.

TABLE III

| | Relative lipolytic activity (%) | |
|---|---|---|
| Concentration of Na deoxycholate (mM) | Pseudomonas spec. DSM 6535 | *Rhizopus arrhizus* |
| 0 | 100 | 100 |
| 0.5 | 114 | 180 |
| 1 | 144 | 160 |
| 2.5 | 177 | 118 |
| 3.5 | 100 | 100 |
| 5 | 60 | 69 |
| 6 | 115 | 64 |
| 7.5 | 117 | 50 |
| 10 | 120 | 0 |

We claim:

1. A method of treating digestive enzyme disorders, which comprises administering to a host in need thereof an effective amount of purified lipase from *Pseudomonas spec.* DSM 6535, which lipase is active at pH 3.5–9.0 and which is not inhibited by about 5–10 mM sodium deoxycholate.

\* \* \* \* \*

UNITED STATES PATENT AND TRADEMARK OFFICE
CERTIFICATE OF CORRECTION

PATENT NO. : 5,645,832
DATED : July 8, 1997
INVENTOR(S) : Braatz, et. al.

It is certified that error appears in the above-indentified patent and that said Letters Patent is hereby corrected as shown below:

Title page, item [62] Division of Ser. No. 170,358, Dec. 28, 1993, Pat. No. 5,489,530, which is the national stage of International application number PCT/EP 92/01412, filed Jun. 23, 1992--.

Signed and Sealed this

Twenty-sixth Day of August, 1997

Attest:

BRUCE LEHMAN

Attesting Officer

Commissioner of Patents and Trademarks